US006304869B1

(12) United States Patent
Moore et al.

(10) Patent No.: US 6,304,869 B1
(45) Date of Patent: *Oct. 16, 2001

(54) RELATIONAL DATABASE MANAGEMENT SYSTEM FOR CHEMICAL STRUCTURE STORAGE, SEARCHING AND RETRIEVAL

(75) Inventors: Jeffrey Moore, Timonimun; Joanne Brazil, White Hall; Jeffrey R. Hoover, Baltimore, all of MD (US)

(73) Assignee: Oxford Molecular Group, Inc., Towson, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/250,440

(22) Filed: Feb. 16, 1999

Related U.S. Application Data

(63) Continuation of application No. 08/883,165, filed on Jun. 26, 1997, now Pat. No. 5,950,192, which is a continuation of application No. 08/715,708, filed on Sep. 19, 1996, now abandoned, which is a continuation of application No. 08/288,503, filed on Aug. 10, 1994, now Pat. No. 5,577,239.

(51) Int. Cl.$^7$ .................................................... G06F 17/30
(52) U.S. Cl. .................................. 707/3; 702/27
(58) Field of Search .......................... 707/3, 100, 102, 707/104; 702/22–27

(56) References Cited

U.S. PATENT DOCUMENTS

| 4,642,762 | * | 2/1987 | Fisanick ..................................... 707/3 |
| 4,811,217 | * | 3/1989 | Tokizane et al. ........................ 707/3 |
| 4,855,931 | * | 8/1989 | Saunders ......................... 395/500.33 |
| 5,025,388 | * | 6/1991 | Cramer, III et al. ........... 364/528.28 |
| 5,056,035 | * | 10/1991 | Fujita ............................... 395/500.33 |
| 5,249,137 | * | 9/1993 | Wilson et al. ................... 395/500.23 |
| 5,367,058 | * | 11/1994 | Pitner et al. ....................... 530/391.9 |
| 5,379,234 | * | 1/1995 | Wilson et al. ................... 395/500.32 |
| 5,386,507 | * | 1/1995 | Teig et al. ............................. 345/348 |
| 5,418,944 | * | 5/1995 | DiPace et al. ............................ 707/3 |
| 5,463,564 | * | 10/1995 | Agrafiotis et al. .............. 364/528.03 |
| 5,577,239 | * | 11/1996 | Moore et al. ............................ 707/3 |

* cited by examiner

Primary Examiner—Maria N. Von Buhr
(74) Attorney, Agent, or Firm—Dickenstein Shapiro Morin & Oshinsky, LLP

(57) ABSTRACT

The present invention is a chemical structure search system and method which expands the capabilities of existing systems by capitalizing on the strengths of relational database technology. The system allows the user to optimally store and search chemical structure information including information relating to multi-valued atoms, multi-typed bonds, Markush searching and various other options in a relational database management system. The system provides a complete chemical information system which includes capabilities for: (1) exact structure searching; (2) substructure searching; (3) key searching; (4) chemical name searching; (5) molecular formula searching; (6) registration of new molecules; (7) structure import/export; and (8) data editing. Additionally, the present invention allows the routine integration of chemical structure data with other related information such as inventory, spectroscopic data and clinical data via standard relational database methods. The system also has dynamic querying capabilities which allow the user to be notified of any new chemicals that are entered into the database that are responsive to previously run queries. Furthermore, structure classes can also be implemented which allow the user to store certain types of information about particular types of chemical structures such as steroids. Accordingly, users can later call up this information in a quick and efficient manner without re-entering or performing previously run queries.

18 Claims, 7 Drawing Sheets

FIG. 1  (S1)
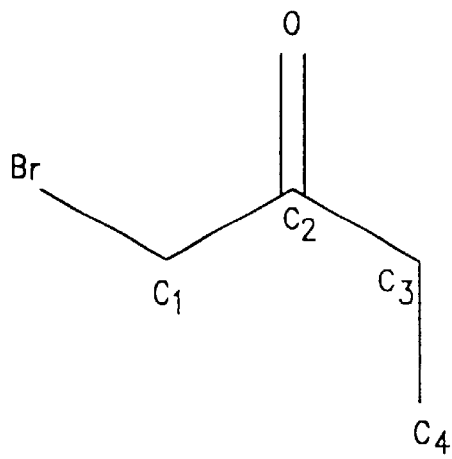
FIG. 2  (S2)
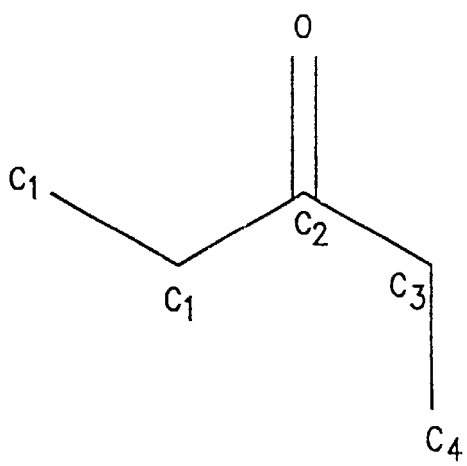
FIG. 3
|   | 1 | 2 | 3 | 4 | 5 | 6 |
|---|---|---|---|---|---|---|
| 1 | $C_1$ | 1 |   |   |   |   |
| 2 | 1 | $C_1$ | 1 |   |   |   |
| 3 |   | 1 | $C_2$ | 2 | 1 |   |
| 4 |   |   | 2 | 0 |   |   |
| 5 |   |   | 1 |   | $C_3$ | 1 |
| 6 |   |   |   |   | 1 | $C_4$ |
1 = SINGLE BOND
2 = DOUBLE BOND

- Cl    a
- Br    b
- C     c
= C     d
= O     e
END OF ATOM    °
WILDCARD       %

FIG. 5  (Q1)

| | |
|---|---|
| Br | Br |
| Br–$C_1$ | Br c • |
| $C_1$–$C_2$ | Br c • c • |
| $C_2$–$C_3$<br>$C_2$–O | Br c • c • ce • |
| $C_3$–$C_4$ | Br c • c • ce • c • |
| O–END | Br c • c • ce • c • • |
| $C_4$–END | Br c • c • ce • c • • • |

# RELATIONAL DATABASE MANAGEMENT SYSTEM FOR CHEMICAL STRUCTURE STORAGE, SEARCHING AND RETRIEVAL

This application is a continuation of U.S. application Ser. No. 08/883,165, filed Jun. 26, 1997, now U.S. Pat. No. 5,950,192, which is a continuation of U.S. application Ser. No. 08/715,708 filed Sep. 19, 1996, now abandoned, which is a continuation of U.S. application Ser. No. 08/288,503 filed Aug. 10, 1994, now U.S. Pat. No. 5,577,239.

FIELD OF THE INVENTION

The present invention relates to a relational database management system that stores, searches and retrieves chemical structure information quickly and easily.

BACKGROUND OF THE INVENTION

Chemical and pharmaceutical industries and chemical-related government agencies commonly maintain large chemical substance databases. These entities often provide structure-searching capabilities in association with such databases. Recently, these organizations have been standardizing their databases using relational database management systems (RDBMS) such as the Oracle Relational Database Management System by Oracle Corporation, World Headquarters, 500 Oracle Pkwy., Redwood Shores, Calif. 94065.

The advantages of integrating chemical structure information into an RDBMS include: a closer integration with other related chemical data, efficiency in both storage and retrieval of chemical structure data, and better access to the chemical structure data by other related applications.

Unfortunately, chemical information systems have traditionally been built using specialized database technology requiring, in many cases, hundreds of thousands of lines of custom computer code. Systems of this type are often both difficult to maintain, and difficult to adapt to changing hardware technologies. These maintenance problems, coupled with a lack of portability of these highly specialized systems, often lead to large investments of time and money being allocated to relatively short-lived systems.

The introduction of relational database technology provides an opportunity to transfer a large amount of the database management responsibility from the specialized database systems described above to a standard widely-accepted technology. However, relational technology has typically not been used as the basis for chemical information systems. This is due to the fact that there are problems inherent in any attempt to cast a chemical structure searching system problem into structured query language (SQL)— the standard language of relational databases. These problems include difficulty in storing and representing chemical structures in a database. No chemical information system has yet been implemented using only relational technology as its database component.

Several systems have attempted to achieve this goal but, as more fully explained below, none have been able to develop a purely relational database management system which is able to search and retrieve chemical structure information easily and quickly.

For example, Molecular Access System (MACCS) and Integrated Scientific Information System (ISIS) are both created by Molecular Design Ltd., MDL Information Systems, 14600 Catalina Street, San Leandro, Calif. 94577. These systems provide a stand-alone chemical information system wherein chemical structures are stored as hierarchical structures. However, these systems require large amounts of custom code, and are not maintained in a relational database. Accordingly, they do not have the advantages of relational technology listed above.

While it is true that these systems can be interfaced to a relational database management system such as the Oracle Database Management System noted above, it must be done using additional custom code and software that converts hierarchical structures to the relational tables needed for such a database. Therefore, it is difficult to incorporate the advantages of relational technology into the MACCS and ISIS systems. Moreover, the conversion software slows down overall performance speed.

In summary, these systems do not provide the advantages and capabilities existing in the present invention.

The present invention overcomes the above-listed problems and additionally has the following advantages: (1) development and maintenance costs will be greatly reduced by using a commercial database package. Accordingly, development efforts and benefits can be more effectively directed toward aspects of system design, and improvements in the underlying database technology will be automatically transferred to the chemical information system. This shift of focus away from database development concentrates the development and maintenance efforts on improving the search strategy and the user interface, which are the highly visible aspects of the system; (2) interfacing with other information systems will be simplified since relational databases are already used to store much of the non-structural chemical data used in research and commercial settings; and (3) portability will be much less of a design drawback since the amount of custom programming is minimal and can easily be adapted to numerous types of technology. Therefore, the portability responsibilities are mostly shouldered by the database manufacturer itself, and not by the developer of the chemical storage system.

SUMMARY OF THE INVENTION

The present invention overcomes the shortfalls in the art by developing a chemical structure search system which expands the capabilities of existing systems by capitalizing on the strengths of relational database technology.

The present invention allows the user to optimally store and search the chemical structure information using various search strategies such as multi-valued atoms, multi-typed bonds, Markush searching and various other options in a relational database management system.

Furthermore, it provides a complete chemical information system which includes modules for:

(1) exact structure searching;
(2) substructure searching;
(3) key searching;
(4) chemical name searching;
(5) molecular formula searching;
(6) registration of new molecules;
(7) structure import/export; and
(8) data editing.

Additionally, the present invention allows the routine integration of chemical structure data with other related information such as inventory, spectroscopic data and clinical data via standard relational database methods to allow better usage of all types of chemical information in both commercial and research settings.

By taking advantage of the data manipulation capabilities of relational technology, this system will also introduce dynamic querying capabilities which will allow the user to be notified of any new chemicals that are entered into the database that are responsive to previously run queries. This provides the functionality of relational views for chemical structure information.

Additionally, structure classes can also be implemented which allow the user to store certain types of information about particular types of chemical structures such as steroids. Accordingly, users can later call up this information in a quick and efficient manner without re-entering or performing previously run queries.

With these and other objects, advantages and features of the invention that may become apparent, the nature of the invention may be more clearly understood by reference to the following detailed description of the invention, the appended claims and the several drawings attached hereto.

BRIEF DESCRIPTION OF THE DRAWINGS

FIG. 1 is a chemical representation of structure 1 (S1);

FIG. 2 is a chemical representation of structure 2 (S2);

FIG. 3 is the connection table for structure 2 (S2) set forth in FIG. 2.;

FIG. 5 is chemical representation of query 1 (Q1);

DETAILED DESCRIPTION OF THE PREFERRED EMBODIMENT

The present invention makes use of standard relational database technology such as that found in the commercial product Oracle which is marketed by Oracle Corporation as noted above. All references to the retrieval and storage of information will be done in a standard relational database, and will use standard procedures for doing so, including structured query language (SQL) commands. The operations and functions of relational databases discussed in this patent application are well known to those of ordinary skill in the database management field. Those operations and functions can be found in numerous texts, including Oracle users' and developers' manuals.

I. Hardware

Figure 9:
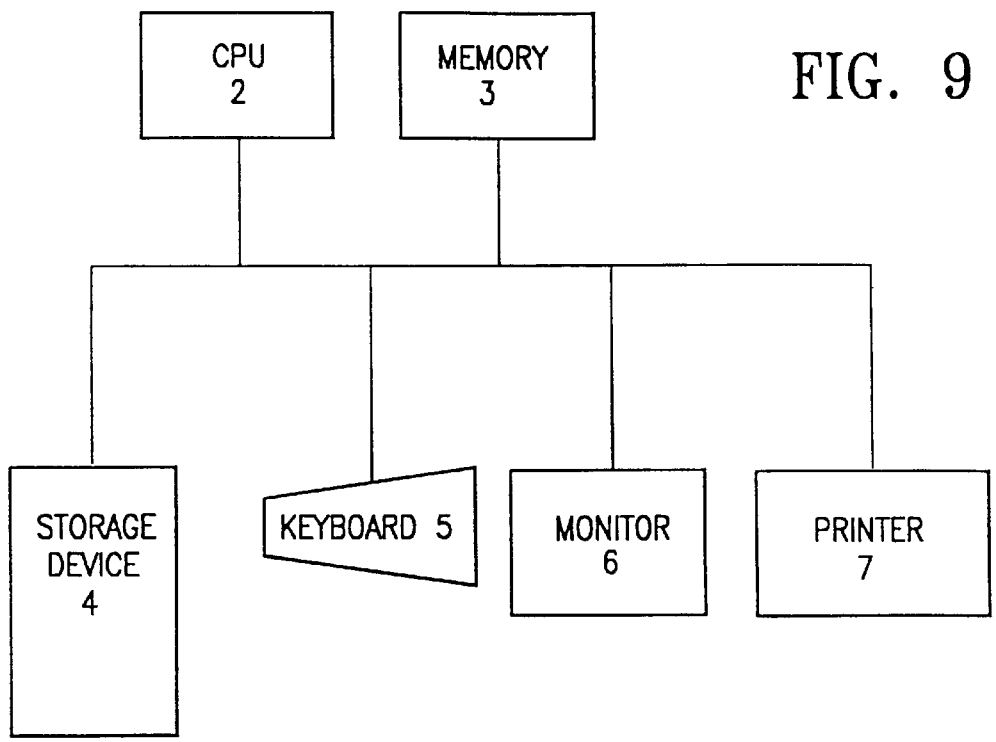
FIG. 9 depicts the hardware configuration of the present invention.

Referring now to FIG. 9, the preferred embodiment of the relational database management system for chemical structure storage and retrieval is shown. A typical computer workstation 1 will contain a central processing unit (CPU) 2, and main memory 3, and can be coupled to storage devices 4 such as magnetic disks, an input device such as a keyboard 5 or mouse, and output device such as a computer monitor screen 6 and a printer 7. One or more such storage devices may be utilized.

The preferred embodiment of the relational database management system for storing, searching and retrieving chemical structure utilizes a microprocessor, such as a Microvax 3100 model 900 operating with a VMS 5.5-2 operating system with at least two gigabytes of disk space and at least 32 megabytes of RAM. The system can be provided with more memory to speed up throughput access rates. The system could also be optionally coupled to a local area network (LAN) or other communications architecture/environment in order to link with other computer workstations and have access to data from other systems.

II. Relational Database Interface

As noted above, one of the advantages of using relational databases for a chemical structure search system is that there is no need on the part of the developers to be concerned with portability, since the relational database is a standard unto itself, that requires no special interface from one type of system to the next.

In the present invention, the use of a standard relational database such as the Oracle Relational Database Management System minimizes the portability issues since they are available on virtually every platform. Additionally, the present invention maintains the degree of portability since it uses standard C with embedded SQL.

III. Registering New Structures

Figure 6:
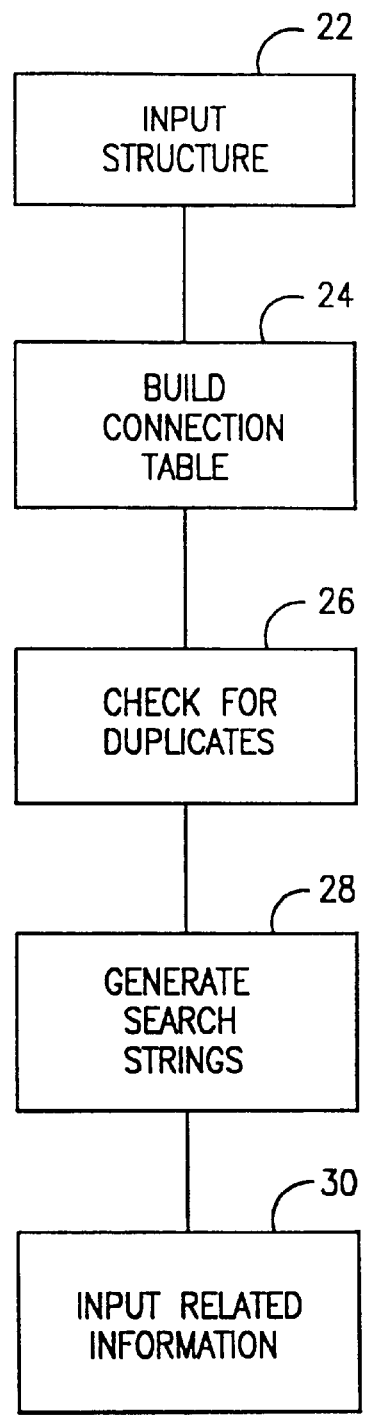
FIG. 6 is a block flow-diagram depicting the registration process.

As shown in FIG. 6, to register a new structure in the database, the user simply enters the atoms and bonds that make up the chemical structure by typing the appropriate keys, or selecting the appropriate choices from menus 22 in a standard chemical drawing software package such as Kekule, marketed by PSI INTERNATIONAL, 810 Gleneagles Court, Suite 300, Towson, Md. 21286.

For each new structure that is registered (added) in the database, several steps must occur: (a) a connection table must be constructed and stored in the database 24; (b) the system verifies that this structure is not a duplicate 26; (c) at least one search key must be created and stored in the database 28, and (d) information such as name, formula and registry key number must be stored in the database 30. Each of these procedures will be fully described below.

a. Construction of a Connection Table

For each structure to be registered in the database, a connection table is constructed at step 24. This table stores information about each atom in the structure including its atomic number, the identity of all of the connected atoms, and the type of bond to each of these connected atoms. For example, the connection table for a chemical structure to be added such as structure S2 as depicted in FIG. 2 is shown in FIG. 3.

The table depicts the types of links that are stored between any two given atoms in a structure. A single bond between two atoms is denoted by a "1" while a double bond is denoted by a "2" and a triple bond is denoted by a "3." This table is stored in a relational table along with its associated registry number in a compressed sparse matrix form. The connection table will be used for the Atom by Atom Matching (ABAM) process which is described more fully below.

b. Search for Duplicates

The system then searches the existing structures to verify that no duplicates exist in the database at step 26. If the structure has already been entered into the system, it will not be entered again.

c. Creation of Search Keys

When a new structure of N atoms is registered in the system, it is necessary to construct N search keys for the structure. These search keys are stored as data in the relational database. Each search key results from a unique numbering of the atoms with a different atom representing the starting point of the key. In effect, N different search keys are stored for each structure of N atoms.

To create effective search keys, it is necessary to derive an unambiguous string of characters for each atom in the structure or query. The string is a representation of the atomic environment of the starting atom. The ordering of characters in the string cannot be sensitive to deletion of portions of the structure or query. That is, deletion can remove portions of the string (with subsequent replacement by wildcards in a query) but cannot cause reordering of the remaining characters in the string. One such algorithm, which builds the string by adding connectivity information using a breadth-first graph traversal is detailed in FIG. 7, and is used in subsequent examples.

Figure 7:
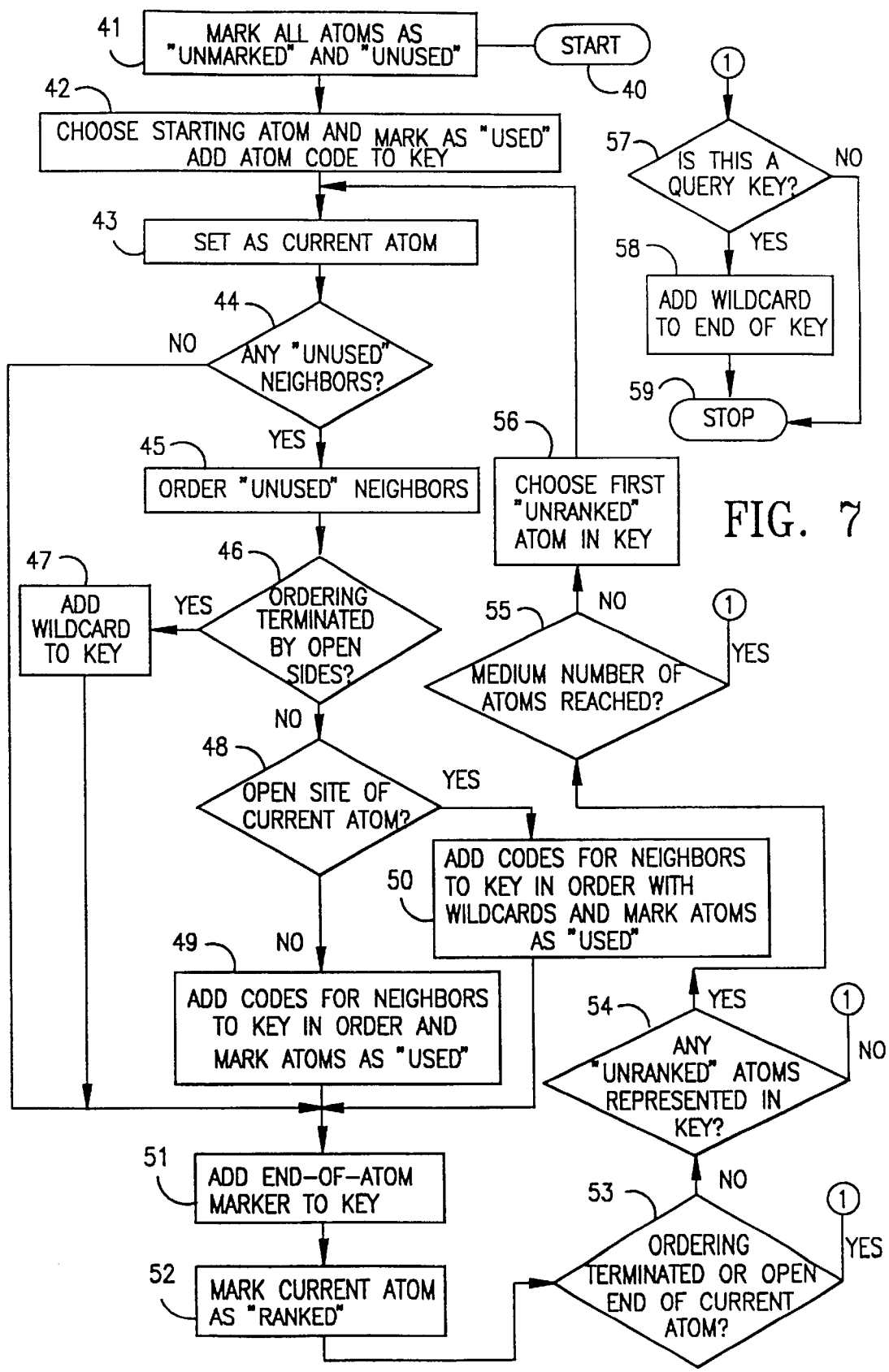
FIG. 7 is a block flow diagram depicting the generation of search keys.

As shown in FIG. 7, for each starting atom, the following process is used to generate a search key. The process starts at step 40, and at step 41 all atoms are marked as "unranked" and "unused". Next, at step 42 the starting atom is marked as "used" and added to the key. Additionally, at step 43, the starting atom is marked as the current atom.

So, for example, when reviewing structure S1 in FIG. 1, and starting with the Bromine (Br) atom, the search string would begin with "Br". For clarity, the first code in the key is shown as the atomic symbol; in practice, a one byte code is used for this purpose. Additionally, the Bromine (Br) atom would be marked as "used" and set to the current atom.

At step 44, any unused neighbors are examined. In this example, the Carbon ($C_1$) atom would be unused and accordingly, the system would advance to step 45 where unused neighbors were ordered. Because there is only one neighbor in this portion of the structure, and the ordering is not terminated by an open site at step 46, and there is no open site at the current atom at step 48, the system advances to step 49, where codes for the neighbors, in order, are added to the key and marked as "used".

In this example, the letter "c" will be added to the key to indicate the single bond to the Carbon ($C_1$) atom, and the Carbon ($C_1$) atom will be marked as "used". The system next adds an end-of-atom marker to the key at step 51. The key now reads "Br c .". The current atom (Br) is marked as "ranked" at step 52.

The system next verifies that ordering was not terminated, and there was no open site at step 53. The process continues at step 54 by examining if any atoms in the key are unranked. In this example, the Carbon ($C_1$) is unranked. Because the key is not too long (i.e., not longer than a predefined length) at step 55, the Carbon ($C_1$) is chosen as the first unranked atom in step 56. The process repeats itself starting at step 43 with the Carbon ($C_1$) atom as the current atom.

Now, the Carbon ($C_1$) is marked as the current atom, and the unused neighbors are examined at step 44. Once again, there is only a single bond to a Carbon ($C_2$) atom, and therefore the ordering at step 45 is unnecessary. At step 49, a "c" is added to the key, and at step 51 the end-of-atom marker is added to the key. Accordingly the key now reads "Br c . c .".

This Carbon ($C_1$) atom is now marked as "ranked" at step 52. Once again, the unranked atoms in the key are examined at step 54, and the first unranked atom in the key is chosen at step 56. This Carbon ($C_2$) is now set as the current atom at step 43, and the unused neighbors are examined at step 44. There are two unused neighbors: a double bond to an Oxygen (O) denoted by "e", and a single bond to a Carbon ($C_3$) denoted by "c". At step 45, these bonds are ordered, with "c" taking precedence over "e". These codes are then added to the key in order, and the atoms are marked as "used" at step 49. Next, an end-of-atom marker is added to the key at step 51. The key now reads "Br c . c . c e .". The Carbon ($C_2$) atom is marked as "ranked", and the unranked atoms (the Oxygen and Carbon ($C_3$) atom) are examined at step 54.

At step 56, the first unranked atom in the key ($C_3$) is chosen, and at step 43, it is set as the current atom. The process continues by examining the single bond to the Carbon ($C_4$) emanating from this Carbon ($C_3$), and accordingly "c" and "." are added to the key. The key now reads "Br c . c . c e . c .".

Figure 12:
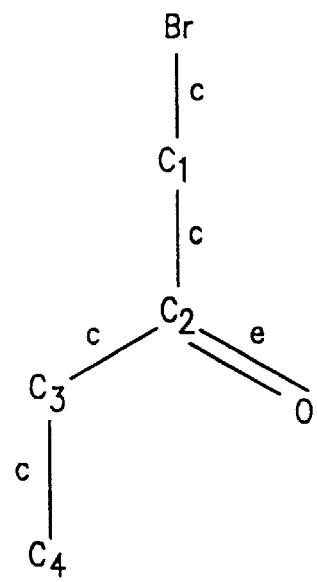
FIG. 12 is a step-by-step generation of a search key for structure S1.

The next unranked atom (Oxygen) is then set as the current atom at step 43. Given that there are no unused neighbors at step 44, an end-of-atom marker is simply added to the key at step S1. The process once again repeats with $C_4$ as the current atom. Because there are no unused neighbors, "." is appended to the string, and the process stops for this starting atom. The final search key would be: "Br c . c . c e . c . . .". The same process is repeated for every starting atom in a given structure. This process is also shown, step-by-step, in FIG. 12. (Steps 57, 58 and 59 in FIG. 7 will be explained in Section V. below.)

Figure 4:
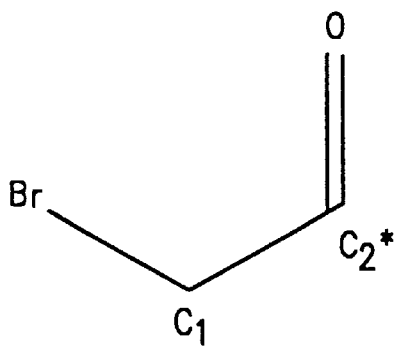
FIG. 4 defines the bonded atom codes to be used in search key and query generation.

Utilizing this key generation algorithm (FIG. 7) with the illustrative bonded atom codes shown in FIG. 4, the keys generated for structure S1 (FIG. 1) are:

1) Br c . c . c e . c . . .
2) C b c . . c e . c . . .
3) C c c e . b . c . . . .
4) O d . c c . b . c . . .
5) C c c . . c e . b . . .
6) C c . c . c e . b . . .

For structure S2 (FIG. 2), the keys generated are:

1) Cl c . c . c e . c . . .
2) C a c . . c e . c . . .
3) C c c e . a . c . . . .
4) O d . c c . a . c . . .
5) C c c . . c e . a . . .
6) C c . c . c e . a . . .

These search keys are stored in the database with associated registry numbers which correspond to the registry numbers of the connection tables and associated information. Keys that are duplicated due to symmetry are eliminated at registration time.

The steps required for processing a search are unaffected by the details of the search key generation process. That is, any key generation process which satisfies the conditions set forth in the opening paragraph of this section (generation of an unambiguous character string for each atom in the structure, etc.) can be utilized without modification of the search engine software.

An additional process, which builds the string by listing structural features found at each graph theoretical distance (level) from the starting atom is detailed below.

Figure 11:
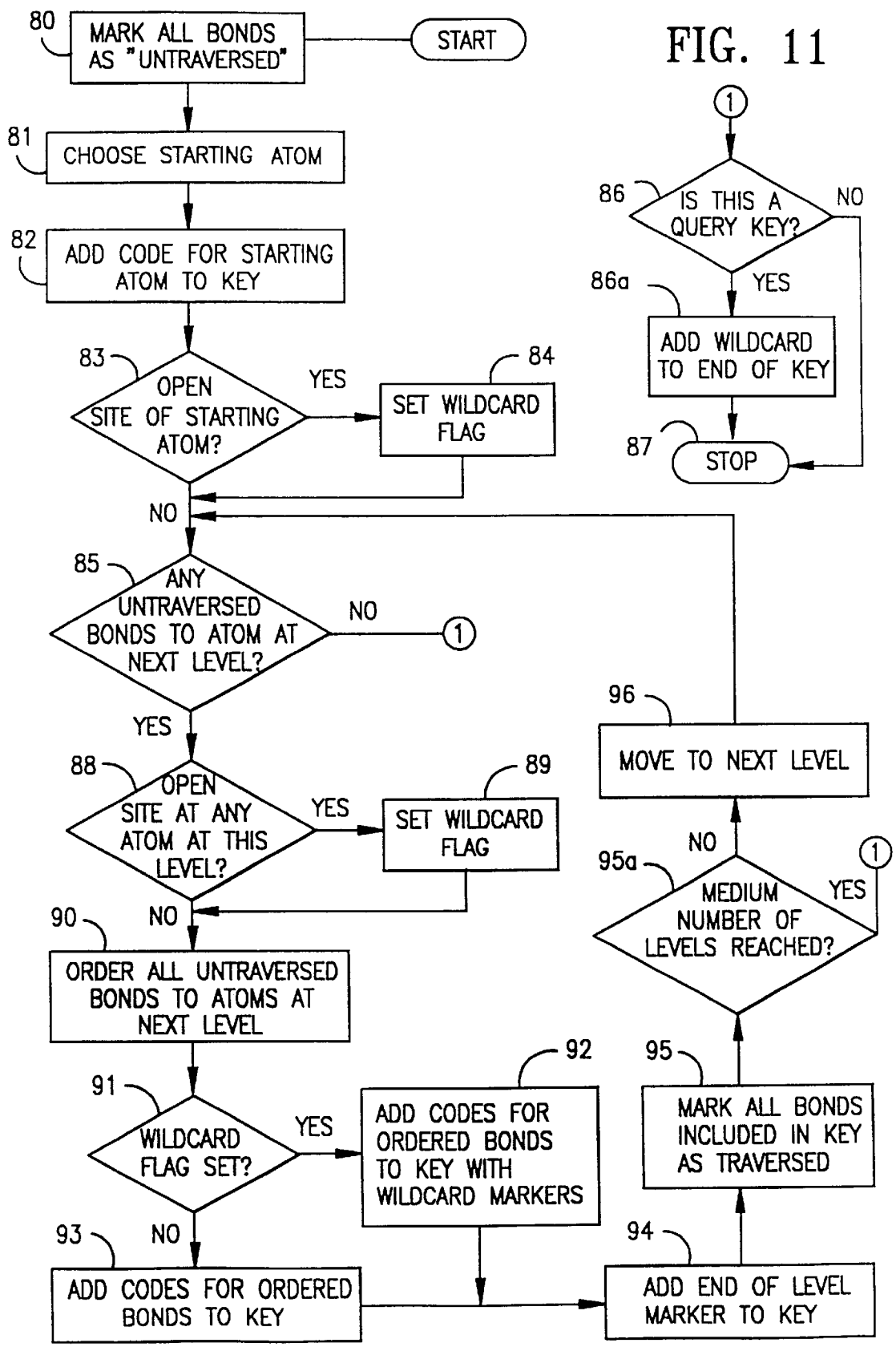
FIG. 11 is a block flow diagram depicting an alternative key generation process.

As shown in FIG. 11, and using structure S1, the following process could also be used to generate search strings. Beginning at step 80, all bonds in a given structure are marked as "untraversed". A starting atom is chosen, which in this case is the Bromine (Br) atom, at step 81, and added to the key at step 82.

Because there are no open sites on this atom, the process continues at step 85, where the system examines if any untraversed bonds to atoms at the next level exist. In this case, there is an untraversed path to a Carbon ($C_1$) atom. The system next determines that there is no open site at any atom at this level at step 88 and, if not, continues at step 90, by ordering all untraversed bonds to all atoms at the next level.

Because the wildcard flag has not been determined as having been set at step 91, the system continues by adding the codes for the ordered paths to the key at step 93. Then, at step 94, the system adds an end-of-level marker to the key. Accordingly, the key now reads "Br c .", and all bonds that are included in the key are marked as "traversed".

The system moves on to the next level with the Carbon ($C_1$) atom at step 96. Once again, the system determines that there are untraversed paths to atoms at the next level at step 85, and ultimately adds "c" and "." to the key, at steps 93 and 94, respectively, after going through steps 88–92.

The system then marks these bonds as "traversed", and moves to the next level beginning with the Carbon ($C_2$) atom. Once again, untraversed paths are found at step 85, namely a double bond to an Oxygen (O) denoted by "e", and a single bond to a Carbon ($C_3$) denoted by "c". These codes are ordered at step 90, and are added to the key with "c" taking precedence over "e" at step 93. Again, an end-of-level marker is added to the key at step 94. The string now reads "Br c . c . c e .".

Next, the system advances to the next level in this structure, and repeats the above process with the Carbon ($C_3$) atom. Once again "c" and "." are added to the string.

Finally, the system moves to the next level at step 96 using the last Carbon ($C_4$) atom. At step 85, the system determines that there are no untraversed paths to atoms at the next level, and stops at step 87. The final key reads: "Br c . c . c e . c .".

d. Associated Information Storage

Additional information about each structure can also be stored in the database, such as registry key or other unique identifier of a structure, name, and formula. The user may also define any additional information to store and search using standard RDBMS technology.

IV. Implementation Issues

Each of the fragment codes comprising the search keys can be made to occupy a single byte in the database. There are approximately 313 of these fragment types existing in a large sample of structures. One byte allows 256 possibilities, three of which cannot be used. (Byte 0 cannot be used due to its importance in programming, and two bytes used in the relational database management system for its wildcard operation cannot be used, since it is normally difficult to search these characters and use the SQL "Like" operator in the same statement).

The remaining bytes can be divided into three groups: (1) those representing the most common fragments, (2) those representing atoms whose presence alone (regardless of bonding) is an effective screen, and (3) those very rare atoms that can be grouped together; accordingly, every search for these atoms is essentially a multi-valued search.

V. Processing of Query Substructure Searches

Performing a query against search keys is a relatively simple matter. Each query structure generates one search key for each atom in the structure that could be assigned an unambiguous fragment code. The search keys of the query structure are generated by applying exactly the same rules to the query structure as those used to generate the database search key defined in III.b. above, with the only exception being treatment of wildcards.

When a wildcard (i.e., a site in which no particular atom is necessary for the search) is encountered, the process must either stop, or continue the query by identifying all possibilities for the value of that wildcard. Additionally, queries can easily accommodate multi-valued atoms and multi-typed bonds or Markush searches in the same way that wildcards are handled. The advantage of this methodology over standard screening techniques is that it reflects the specificity of the query. For moderately specific queries (i.e., few wildcards), it enables remarkable selectivity because of the length of the key.

As demonstrated with the generation of search keys above, the basis of the search process is that the search keys are generated using one unambiguous set of rules. So long as these rules are applied to the query structure in exactly the same fashion, and since each database structure has a key originating from each of its atoms, the results will be standardized.

In order for the database structure to match the query structure, every search key generated for the query must match one or more search keys generated for the database structure. Additionally, if any query search key fails to retrieve the structure, the query cannot be a substructure of that structure. These rules make it possible to perform this extremely selective screening process in a relational database with a single SELECT statement.

To generate a query, the user types in a structure in the same way that new structures are entered, and can indicate where there are wildcards (i.e., no particular atom necessary) and where there are multiple acceptable types of atoms or bonds by indicating the specific atoms and bonds that are acceptable in any given position.

As noted above, the query keys are generated in the same manner as the search keys for the structures. Accordingly, any acceptable key generation process may be used. Therefore, when generating a query key for Q1 in FIG. 5, and using the process shown in FIG. 7, the following steps occur.

The process begins at step 40, and at step 41, all atoms are marked as "unranked" and "unused". A starting atom is chosen and marked as "used", and the atom code is added to the key at step 42. In this example, the Bromine (Br) atom will be the starting atom.

At step 43, Bromine (Br) is marked as the current atom, and at step 44, it is determined that there are unused neighbors. The process continues at step 45, with all unused neighbors being ordered.

Because there are no open sites at step 46, and because there is no open site at the current atom at step 48, the codes for the neighbors are added to the key in order and are marked as "used" at step 49. The process continues with an end-of-atom marker being added to the key at step 51. The key now currently reads "Br c .", and the Bromine (Br) atom is marked as "ranked" at step 52.

Because the ordering was not terminated, and no open site was found at the current atom at step 53, the process continues at step 54 by reviewing the unranked atoms represented in the key. The system next verifies that a maximum number of atoms has not been reached (the length of the query key does not exceed a predetermined maximum length), and the first unranked atom ($C_1$) is chosen at step 56.

The process continues at step 43 with the Carbon ($C_1$) atom being set as a current atom. Again, all unused neighbors are examined at step 44, and ordered at step 45. Because the system has still not encountered an open site, the code for this bond (single bond to a Carbon) is added to the key at step 49, with the end of atom marker added to the key at step 51. The query key now reads "Br c . c .", and $C_1$ is marked as "ranked".

The process next repeats itself with $C_2$ as the first unranked atom in the key at step 56. Accordingly, $C_2$ is marked as the current atom at step 43, and at step 44 it is determined that there are still "unused" neighbors. The unused neighbors are attempted to be ordered at step 45. The bonds of the neighbors consist of a double bond to an Oxygen (O) denoted by "e", and a wildcard (*).

The ordering is not terminated by the open site at step 46, because open sites only terminate this process at step 46 if the open site does not exist on the current atom. Because the open site exists on the current atom, the "yes" branch is taken at step 481 and at step 50, codes for the neighbors are added to the key with wildcard symbols around them. Next an end-of-atom marker is added to the key at step 51. Accordingly, the current string reads "Br c . c . % e %"; and the $C_2$ atom is marked as "ranked."

At step 53, because an open site was found at the current atom, the system advances to step 57. This string is a query key, so a wildcard is added to the end of the key at step 58, and the process is stopped at step 59. Accordingly, the final string reads "Br c . c . % e % . %". The process is then repeated with all other atoms as starting atoms.

Utilizing the key generation process (FIG. 7) with the illustrative bonded atom codes as shown in FIG. 4, the keys generated for query Q1 (FIG. 5) are:

1) Br c . c . % e % . %
2) C b c . . % e % . %
3) C % c % e % . %
4) O d . % c % . %

The process illustrated in FIG. 11 can also be used to generate query strings. The only notable addition would be that when an open site is encountered at step 83 or 88, a wildcard flag is set at steps 84 or 89, respectively. Then, from step 91, the system advances to step 92, and adds wildcard (%) symbols before and after every code to be added to the string at this step. Additionally, a wildcard (%) symbol is added to the end of the string.

When a match exists between a query and a given structure, each of the query keys will match one or more of the search keys of the structure. Therefore, any one of the query keys may be used to retrieve a matching structure. Statistical information is stored in the database allowing the optimal query key to be used as the primary screen.

However, passing the screening phase alone is not enough to indicate that a match has been found. The system must next verify that the query structure is a subset of the structure by performing an atom by atom matching (ABAM) process. To do this, a connection table is prepared for the query structure in the same way that it is prepared for the newly registered structures in III.a. above (see FIG. 3). These two connection tables are then compared atom by atom, bond by bond. If every atom and bond in the connection table for the query is found in the connection table for the structure, the system returns a match.

Three cases are possible.

Case 1. The query is a substructure of the retrieval structure. Note that Q1 (FIG. 5) is a substructure of S1 (FIG. 1). In this case, note that each Q1 key matches an S1 key (Q1 keys 1, 2, 3, 4 match S1 keys 1, 2, 3, 4 respectively).

Case 2. The chosen key may retrieve a structure for which the query is not a substructure. For example, Q1 key 4 would match S2 key 4 even though Q1 is not a substructure of S2. However, the ABAM would eliminate this structure.

Case 3. The chosen query key does not match any of the keys of a particular structure. For example, Q1 key 1 does not match any of the keys of S2. Therefore, S2 is eliminated as a match and ABAM is avoided.

Although one query key is typically used to drive the screening process, the other query keys can be used a secondary screen. In Case 2 above, using Q1 key 1 as a secondary screen would eliminate S2, thus avoiding ABAM.

The query, along with the matching results and other identifying information (such as owner of query and name of query), are stored in the relational database for later use and viewing.

Figure 10:
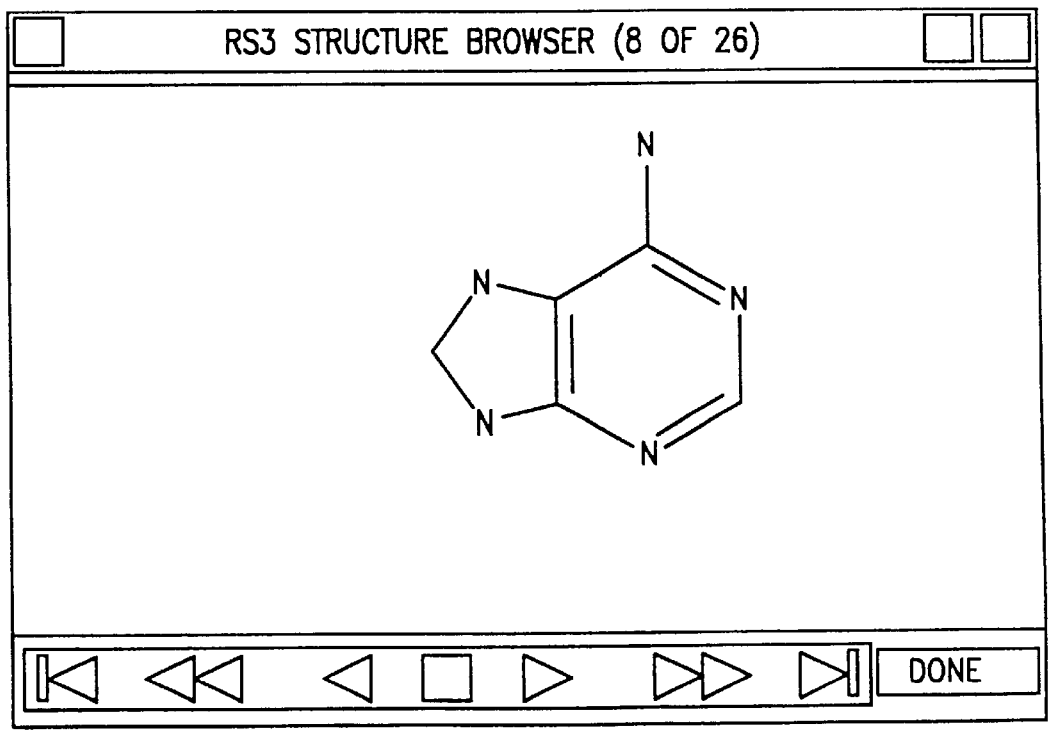
FIG. 10 depicts the screen for viewing results of queries.

The user may simply then advance through and view all of the structures that are a match in the system which are displayed on a screen, such as that shown in FIG. 10. If no structures match, the system will return a message indicating this.

Due to the fact that most of the work is done during the initial screening phase (comparing query strings to structure search keys), the time-consuming atom by atom matching is done only on a relatively small subset of the total structures in the database. Accordingly, this methodology may be much quicker than other systems which perform the same function.

Because all search queries and results are stored in the relational database, the user, through standard relational database procedures, may also list previously conducted searches, edit previously defined searches, update or refresh previously run searches, view structures in any search, and delete previous searches.

VI. Exact Structure (Identity) Searching

Identity searching involves finding a particular structure within a set of database structures. This operation is performed by users, and is also needed at the time of registration. Typically, this means finding a structure in the database that matches the query exactly. An identity search is a special case of the substructure search outlined above, but having no open sites in the query.

Thus, the current substructure search method described above is an adequate method for implementing identity searching, and as such will be used accordingly. Additionally, the meaning of "exact match" can be user-definable. The default definition limits the matching process to element types and bonding. Users can also specify additional structural information such as charge and mass values. This is performed at atom by atom matching time.

VII. Chemical Name Searching

Chemical name searching has been a problem of special note in the field of chemical information systems. Most chemical names are long and complex strings which are not easily searchable by standard substring searching mechanisms. This problem is compounded by the fact that most chemicals are known by many systematic and/or trade-names.

Chemical name searching can be accomplished by storing and indexing carefully defined name fragments, as well as indexing the complex strings of the complete chemical names. Searching can be performed on a partial or complete chemical name query using standard relational database technology.

To optimize the search, the query is degenerated into its constituent chemical terms. The terms are sorted in ascending order by frequency of occurrence found by looking up the number of compounds having a particular term in a stored table. This stored table is created by scanning all names of structures upon registration, and storing frequency information in that table. Thus, this table acts as an index to chemical name fragments.

Given this list of chemical terms, the search can be performed by intersecting the resulting SELECT statements or using one to drive a correlated subquery.

Since the chemical name information is handled entirely by the relational database, the data is then easily integrated with the rest of the chemical information.

VIII. Molecular Formula Searching and Key Searching

Molecular formula can be done by using standard SQL string search methods on all or part of the formula. Key searching (lookup by identifier) is a standard SQL operation.

IX. Data Integration and Import/Export of Data

A significant advantage of basing a chemical information system in a relational database is the ease with which the structure data can be combined with related data, resulting in a complete, integrated system. This allows information in other systems to be easily imported and exported into the RDBMS using standard RDBMS functionality.

X. Dynamic Queries

As is true with all relational databases, the design of the system decomposes into a series of entities, relationships, and functions. The relationships among entities are rigorously defined since referential integrity is the cornerstone of relational database design. A chemical information system implemented using relational technology must be designed with these considerations in mind.

A natural relationship exists between the database structures and the resulting substructure searches with each search resulting in a set of compound identifiers. In the present invention, a relational table is used to store the set of identifiers during each search of the database. This is implemented by creating a table to store general information about the query (current user, date, query structure, options and search statistics). A related table is created to store the identifiers of those structures matching the query.

As new structures are registered in the system, the set of structures identified as resulting from earlier queries becomes obsolete since the structure database contains structures not present at the time of the original search. This is, in a sense, a violation of referential integrity because the relationship between structures and queries are not maintained.

In the present invention, however, the concept of dynamic queries is introduced. When a new structure is registered, the system will examine those queries designated as dynamic, and will add the identifier to the search result set for each query matching the new structure. This process, made simple by relational technology, allows the system to offer functionality never before available in chemical information systems.

Dynamic queries are analogous to relational views. That is, they allow searches of the database to be stored as objects in the database that are always current. The following example will illustrate the type of functionality made possible by dynamic queries.

Figure 8:
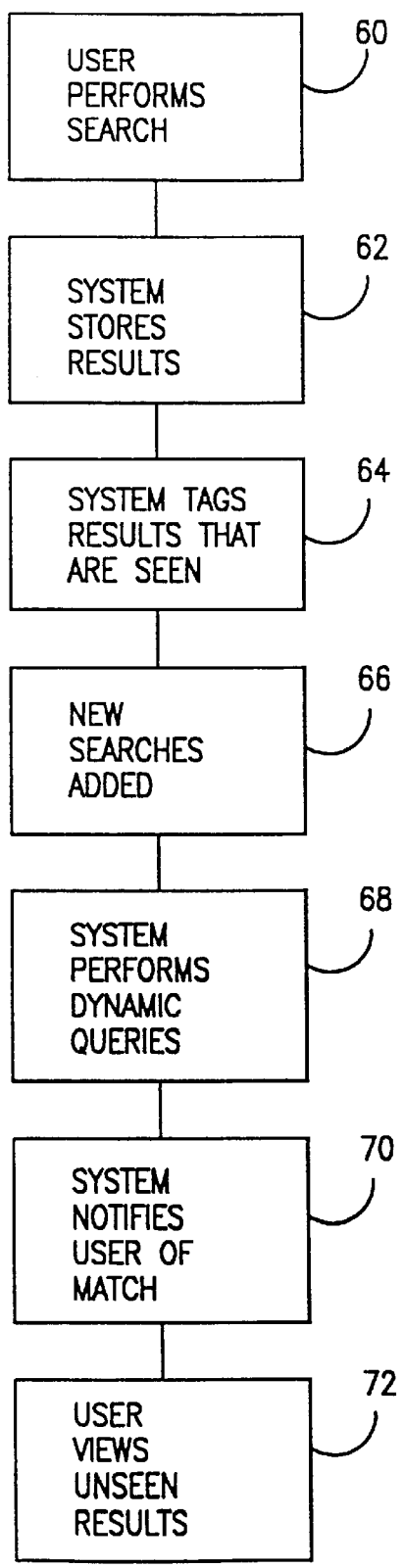
FIG. 8 is a block flow diagram depicting the operation of dynamic queries.

As shown in FIG. 8, when a user performs a search at step 60 (substructure, chemical name, molecular formula), the system stores the resulting set of compound identifiers at step 62. As the user examines these compounds, the system flags each compound as having been viewed by the user at step 64. Therefore, the system always knows the search results, and the extent to which the user has reviewed them.

A user interested in a particular class of structures (e.g., steroids) would perform a search once and designate the search as dynamic. Thereafter, the search will be maintained automatically by the system. In fact, the system would notify the user whenever a new steroid was registered in the system at step 66. This is done by having the system perform all dynamic queries on any newly registered molecule as it is registered into the database at step 68 and notifying the user if a match occurs at step 70. The user could then view the previously unseen results at step 72 without having to repeat the query or view previously seen results.

While dynamic queries would not have much importance with relatively static databases, they would have many uses in the system serving a research environment. Heavy use of dynamic queries could require allocation of significant amounts of disk space for storing search results. Additionally, the performance of the registration process could be adversely affected by the presence of a large number of dynamic queries.

These potential problems can be controlled by the introduction of a resource allocation system with each user being assigned two quotas. The first quota controls the number of dynamic queries that the user can have active at any one time, which will protect performance at the time of the registration process. The second quota will control the total number of structure identifiers that each user has stored by dynamic queries to conserve disk space.

Alternatively, users would be allowed to disable these quota systems, but this may slow the system during the registration process, or may exhaust disk space for the database.

XI. Structure Classes

The division of chemical structures into classes based on overlapping criteria (e.g., functional groups, ring systems) have long been used as an organizational technique in chemistry. Chemical information systems typically provide for this class system by allowing users to intersect the results of different searches. While this intersection is a necessary feature of any chemical information system, it does not address the fundamental importance of the classification schemes used in chemistry. In the present invention, a mechanism will be provided for maintaining any number of classification schemes in the database for structures. These schemes or structure classes can be privately defined by individual users, or can be used as a system-wide search aid.

A "structure class" is defined to be a set of structure identifiers resulting from a substructure search, a chemical name search, a molecular formula search, or by a combination of these searches. Structure classes are an application of dynamic queries used to limit the scope of future searches. For example, the system may maintain a structure class for steroids. When a user performs a search, he or she can designate that the result should be restricted to the members of the steroid class. Accordingly, the user could simply query the database for all steroids that have a particular substructure without drawing the entire steroid ring.

This results in two primary benefits: The first benefit is that queries are simplified, i.e., there is no need to draw complex queries, and the second benefit is that the screening phase need only be applied to those compounds already known to be members of the structure class.

Dynamic queries and structure classes both exhibit a common benefit—the overhead involved in structure searching is encountered only once (when the dynamic query or structure class is defined) and additional overhead is distributed evenly across subsequent updates to the chemical structure database.

From the preceding description, it is evident that the invention has been described in detail by reference to a particular embodiment adapted for use in the field of chemistry. Although this invention offers many advantages in this field, it may be used in other fields wherein structure data is stored advantageously as well. Accordingly, this invention is not intended to be limited by the details of the preferred embodiment described above, but rather by the terms of the appended claims.

What is claimed is:

1. A method for storing chemical structures in a relational database, comprising:

receiving the atoms of a chemical structure;

receiving the bonds between the atoms of said chemical structure;

constructing a matrix representation of said chemical structure including said atoms and said bonds;

storing said matrix in said relational database;

generating a search key for said chemical structure;

said step of generating a search key further comprising the step of marking all atoms as "unranked" and "unused"; and storing said search key in said relational database.

2. The method of storing chemical structures of claim 1, further comprising:

defining a registry key number for said structure;

defining a registry key name for said structure; and storing said registry key number and said registry key name in said relational database.

3. The method of storing chemical structures of claim 1, further comprising storing a chemical formula for each said chemical structure in said relational database.

4. The method for storing chemical structures in a relational database according to claim 1, further comprising relating inventory information to said stored structure.

5. The method for storing chemical structures in a relational database according to claim 1, further comprising relating spectroscopic data to said stored structure.

6. The method for storing chemical structures in a relational database according to claim 1, further comprising relating clinical or biological information to said stored structure.

7. A method for searching chemical structures stored in a relational database, comprising:

inputting at least one query which may include atoms and/or bonds;

generating one query key for said inputted query;

said step of generating one query key further comprising the step of marking all atoms as "unranked" and "unused";

creating a query connection table derived from said inputted query;

comparing at least one said query key to one or more search keys for a given database structure, wherein a match is found when said at least one said query key matches at least one of said search keys corresponding to said chemical structure;

comparing said query connection table to a search connection table when said match is found;

creating a table which stores said matches of said comparisons; and outputting the results of said inputted query.

8. The method of searching chemical structures stored in a relational database according to claim 7, wherein said step of generating at least one query key comprises assigning a code to each atom in a structure, said code being based on the type of atom and the type of neighboring atoms.

9. The method of searching chemical structures stored in a relational database of claim 8, further comprising:

labeling each bond with a unique letter based on an ordering of said bonds; and storing said letters as a search key in said relational database.

10. The method of searching chemical structures stored in a relational database according to claim 7, wherein said search key includes a Markush searching query.

11. The method of searching chemical structures stored in a relational database according to claim 7, wherein said search key includes a wildcard search query.

12. A method of storing chemical structures in a relational database, comprising:

inputting at least one structure including atoms and bonds into a relational database of a computer;

marking all atoms in said at least one structure as "unranked" and "unused";

constructing a matrix representation of each of said at least one structure including said atoms and said bonds;

checking stored structures for duplicates;

generating one search key for each of said atoms and said bonds in said structure; and storing said search keys in said relational database.

13. The method of storing chemical structures of claim 12, further comprising:

defining a registry key number for said structure;

defining a registry key name for said structure; and storing said registry key number and said registry key name in said relational database.

14. The method of storing chemical structures of claim 12, further comprising storing a chemical formula for each said structure in said relational database.

15. The method for storing chemical structures in a relational database according to claim 12, further comprising relating inventory information to said structure.

16. The method for storing chemical structures in a relational database according to claim 12, further comprising relating spectroscopic data to said structure.

17. The method for storing chemical structures in a relational database according to claim 12, further comprising relating clinical or biological information to said structure.

18. The method of storing chemical structures stored in a relational database according to claim 12, further comprising relating inventory data to said stored structure, wherein said inventory data is selected from the group consisting of spectroscopic data, clinical data, toxicological data and biological data.

* * * * *